United States Patent [19]

Vining et al.

[11] Patent Number: 4,909,793
[45] Date of Patent: Mar. 20, 1990

[54] INTRAVENOUS CATHETER APPARATUS WITH RETRACTABLE STYLET

[76] Inventors: Herbert C. Vining, Rte. 1, Box 399HV, Patterson, La. 70392; Clara G. Ryan, 10 Trepagnier, Destrehan, La. 70047

[21] Appl. No.: 238,536

[22] Filed: Aug. 29, 1988

[51] Int. Cl.⁴ .............................................. A61M 5/00
[52] U.S. Cl. .................... 604/164; 604/197; 604/198; 128/763
[58] Field of Search ........ 604/164, 162, 192, 195–198, 604/263; 128/763

[56] References Cited

U.S. PATENT DOCUMENTS

| | | | |
|---|---|---|---|
| 4,702,738 | 10/1987 | Spencer | 604/243 X |
| 4,747,831 | 5/1988 | Kulli | 604/110 |
| 4,762,516 | 8/1988 | Luther et al. | 604/164 |
| 4,772,265 | 9/1988 | Walter | 604/164 |
| 4,781,692 | 11/1988 | Jagger et al. | 604/164 |
| 4,813,936 | 3/1989 | Schroeder | 604/263 X |

Primary Examiner—Dalton L. Truluck
Attorney, Agent, or Firm—Pravel, Gambrell, Hewitt, Kimball & Krieger

[57] ABSTRACT

The present invention provides an intravenous catheter apparatus having a retractable stylet, comprising a cannula member positioned at the end of a catheter, affixed to an end portion of a stylet body and engaged to an end portion of a tubular stylet protector chamber. The stylet protector chamber includes a stylet body plunger member having a stylet body and stylet on the distal end thereof, the stylet insertable in the bore of the cannula, and extending past the distal end of the cannula when the stylet is in the full extended position.

11 Claims, 2 Drawing Sheets

INTRAVENOUS CATHETER APPARATUS WITH RETRACTABLE STYLET

BACKGROUND OF THE INVENTION

1. Field of the Invention

The apparatus of the present invention relates to intravenous catheters. More particularly, the present invention relates to an intravenous catheter apparatus which incorporates a stylet which may be retractable into the barrel of the protector chamber after use for safe disposal of the stylet after contamination.

2. General Background

In the area of providing health care, one of the most difficult problems raised by concerns of health care providers is the technology that is acquired in order to insure a safe hospital environment. Members of hospital staff, more particularly members of a hospitals medical staff, want to be assured that the risk of becoming infected nosocomially while caring for patients is minimized as much as possible. In addition, patients want assurances that treatments in hospitals do not put them at risk. This concern is including but not limited to the hospital setting but encompasses nursing homes, home health, dentist and physician practice and hospice care.

There have been two basic approaches which achieve to minimize the risk of infection in such settings, those being: (a) the use of protective barriers and (b) testing for infectious processes. The risk of infection from patient to staff is a reality and a great concern to health care providers.

Parenteral transmission, either in the form of needle sticks or in IV stylet puncture wounds is a very common infection route which is of grave concern to intravenous therapy administrators.

At the present time the most prevalent method of preventing puncture wounds and exposure for intravenous therapy implementation as recommended by A.H.A., the C.D.C. and Occupational Safety and Health Administration relies on the use of "universal precautions"; protective barriers such as gloves to protect hands from exposure to blood and/or body substances and containers for disposal of stylets and sharps. Gloves should reduce the incidence of blood contamination of hands, but they cannot prevent penetrating injury caused by needles, stylets, or other sharp instruments.

"Universal precautions" provide a guideline to benefit employees for protection and minimize the risk of nosocomially transmission. However, the effectiveness of such precautions depends on accountability, direct initial orientation, ongoing education, training and vigilant compliance. Presently, it appears that the major concern is the technique by which the precautions are undertaken, but not the technology which would combat such serious injury. On the issues of the likelihood of transmission of nosocomially infection i.e., HIV transmission (Aids), Hepatitis, the C.D.C. sites (four studies of health care worker contracted HIV infection from known percutaneous or mucous membrane exposures. Although the statistics are small, the results of such are catastrophic.

The utilization of an intravenous catheter utilizing a stylet/catheter is the most widely used apparatus in health care today in the field of IV therapy. The problem area is following the puncture of the vascular system with the typical intravenous catheter which contains a sharp stylet which must be extracted from the outer catheter following intravenous insertion, which results in a risk of "puncture wound" or blood contamination following such retraction from the contaminated stylet, which can result in serious nosocomial infections. It is quite apparent that the present method used to combat such puncture injury/contamination is ineffective and the subsequent expenses should employees become injured or contaminated is a serious problem within the health care industry and must be addressed by both health care providers and institutions.

There have been a number of patents issued in the art which relate to technology in the area of syringe design or the like. The most pertinent of these are listed in the accompanying submission of art documents.

SUMMARY OF THE PRESENT INVENTION

The present invention provides an intravenous catheter apparatus having a retractable stylet, comprising a cannula member positioned at the end of a catheter, affixed to an end portion of a stylet body, and engaged to an end portion of a tubular stylet protector chamber. The stylet protector chamber includes a stylet body plunger member having a stylet on the distal end thereof, the stylet insertable in the bore of the cannula, and extending past the distal end of the cannula when the stylet is in the full extended position. There is further provided a plurality of stop members in the bore of the chamber, where lockingly engaging the stylet body in the full extended position. Following insertion of the stylet and cannula into the patient, the stylet body portion and stylet is retracted rearwardly, and the stylet retracted into the bore of the protector chamber, where the stylet body is locked between an additional series of stops, to insure that the stylet remains in the retracted position. Following the retraction of the stylet, the plunger is disengaged from the stylet body and removed from the protector chamber, and cap members are placed on both ends of the protector chamber so that the chamber, housing the stylet in its bore, may be disposed of safely. There is further provided a guide rail for achieving alignment between the bevel surface of the stylet and the guide rail when the guide rail is in the uppermost position along the body of the chamber. Further, there may be provided an additional or an alternative cap member which would house the stylet and cannula prior to or after use of the stylet in the intravenous process.

Therefore, it is a principal object of the present invention to provide an intravenous catheter having a retractable stylet and disposal system in a single unit for achieving easy disposal and protection to the user;

It is a further object of the present invention to provide a stylet which results in no exposure after insertion and/or medication administration, thus eliminating self-/infliction via the stylet puncture due to the retraction properties of the unit;

It is still a further object of the present invention to provide a safety disposable stylet which can not be reused once the plunger is removed from the protector chamber barrel. Thus eliminating inadvertent reuse and destruction of the stylet;

It is still a further object of the present invention to provide a pre-connected system for promoting the decreased risk of contamination for both patient and intravenous therapy administrators and insuring sterility and efficiency while maintaining integrity from preparation to disposal;

It is still a further object of the present invention to provide an intravenous catheter system which is time saving, and reduces preparation time and action expenditure per procedure due to the single unit disposer;

It is still a further object of the present invention to provide a fast and easy system, for which is quickly accessible, accurate, and is utilized like a standard apparatus;

It is still further object of the present invention to provide a stylet and an intravenous catheter having a protector chamber and detent device for preventing displacement of the stylet and eliminating accidental retraction of the stylet and catheter during insertion due to the detent mechanism in the protector chamber; and It is still a further object of the present invention to provide an intravenous catheter with retractable stylet which is used a single time and discarded and is sterile and non-pyrogenic.

BRIEF DESCRIPTION OF THE DRAWINGS

For a further understanding of the nature and objects of the present invention, reference should be had to the following detailed description, taken in conjunction with the accompanying drawings, in which like parts are given like reference numerals, and wherein.

DETAILED DESCRIPTION OF THE PREFERRED EMBODIMENT

The apparatus of the present invention is an apparatus which is used to provide intravenous insertion and/or injection to a patient, and in general in the present state of the art, it would include a catheter attached to the end of a stylet body with the catheter having a cannula, with a stylet inserted through the cannula. In operation, the stylet or the point of the stylet would pierce the skin of the patient with the stylet and the cannula body being inserted into the patient. After a flow is achieved in the bore of the stylet, it is removed from the patient, and the cannula would remain in the patient's vascular system and would have attached thereto a source of fluids or medications which would be administered intravenously into the patient. In general the cannula portion would include a cannula body with a flexible stem portion, which with the flexible stem portion being that portion of the cannula inserted into the body. The present invention would operate in the same manner, with the exception that following the insertion of the stylet and cannula into the patient, the stylet is retracted back into the protector chamber, and the protector chamber is capped so that no contact would be made with the stylet after it has been used in the patient. Therefore, there could be no chance of contracting a disease or injury through an inadvertent puncture with a contaminated stylet.

Figure 1:
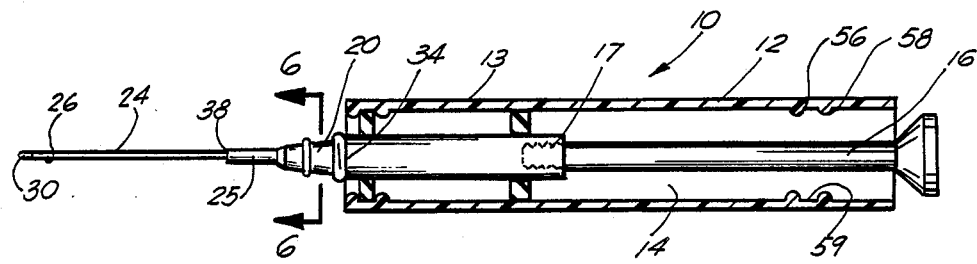
FIG. 1 is an overall side view of the preferred embodiment of the apparatus of the present invention with a stylet and catheter in a fully extended position.
Figure 2:
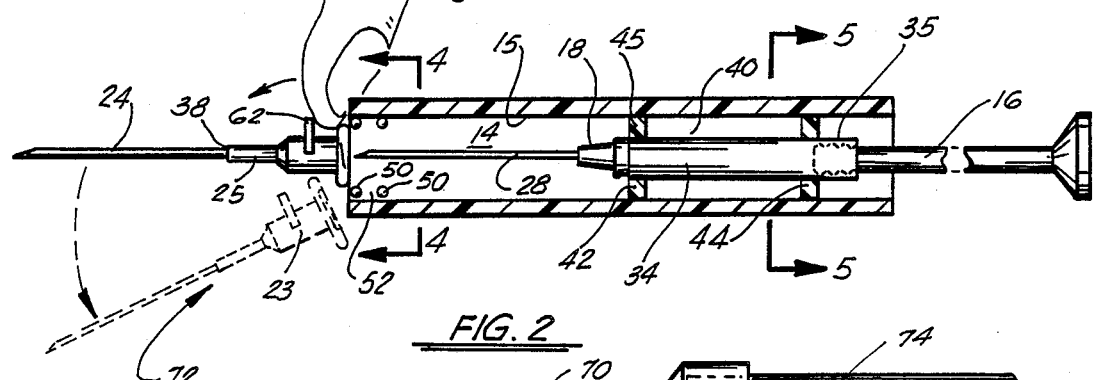
FIG. 2 is an overall side view of the preferred embodiment of the apparatus of the present invention with the stylet in the fully retracted position.
Figure 7:
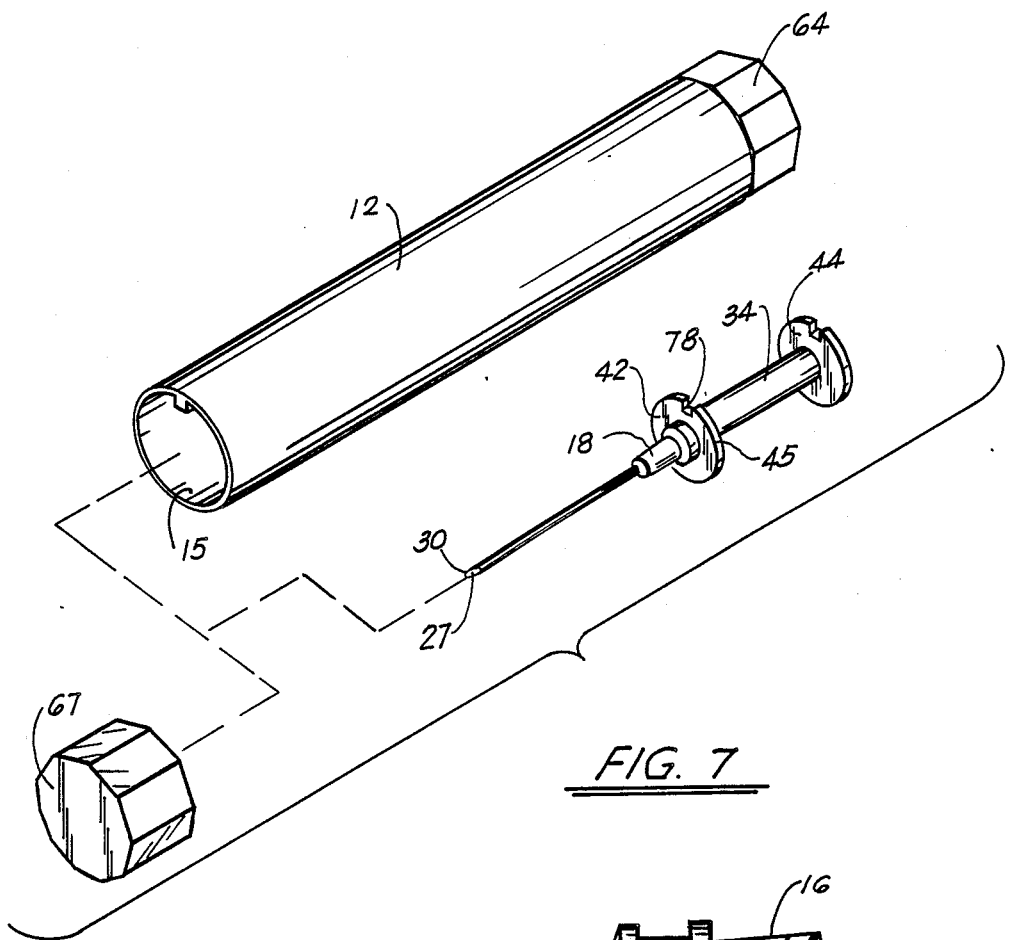
FIG. 7 is an exploded view of the protector chamber body, and the stylet which would be positioned in the body when fully retracted including cap members for sealing the ends open body portion.

The apparatus of the present invention is illustrated by the numeral 10 in FIGS. 1–7. As illustrated in the FIGURES, intravenous catheter apparatus 10 includes a protector chamber portion 12 having a continuous sidewall 13; chamber 12 defining an interior bore 14, throughout its length for the movement of stylet body 34 and stylet body plunger 16 therethrough, as illustrated in FIGS. 1 and 2. As illustrated in FIG. 7, stylet body 34 includes a tapered end portion 18, for frictionally engaging a catheter 20 thereunto as illustrated in FIG. 1, so that catheter 20 would be securely engaged to the end portion 18 of stylet body 34 during use. Catheter 20 would include a flexible cannula portion 24 extending from the body portion 25 of catheter 20, catheter 20 having an open end 26 through which a stylet 28, as illustrated in FIG. 2 would extend therethrough, so that in the fully extended position, as seen in FIG. 1, the end portion 30 of stylet 28 would protrude out the end of cannula 26, for insertion into a patient.

As further illustrated in the FIGURES, catheter 20, in combination with protector chamber 12 would include a means for retracting the stylet 28 into the bore 14 of chamber 12 following the insertion of the stylet into the patient. As illustrated in FIG. 2, this means would include, the stylet body 34, having at its distal end a receiving chamber 35. Receiving chamber 35 would threadably accommodate plunger 16 via threads 17, at its distal end, as illustrated in FIGS. 1 and 2. As was stated earlier, stylet body 34 would include on its forward end, the first tapered end portion 18, to which stylet 28 is attached thereto at point 38. Stylet body portion 34 would be of a substantially less diameter than bore 14, and therefore there would be defined an annular space 40 between the inner wall 15 of protector chamber 12, and the stylet body 34. In order so that stylet body 34 is mounted centrally within bore 14, there would be provided a pair of disc rail guides 42 and 44 respectively. Each of the discs 42, 44 would be mounted around the forward and distal ends of stylet body 34. The outermost wall 45 of each disc 42 and 44, would be in slidable contact with the inner surface 15 of protector chamber 12, so that as stylet body 34 with stylet 28 mounted on its forward end, and plunger 16 mounted on its distal end, moves within bore 14, stylet 28 would be centrally located within bore 14, and be received into the bore of cannula 24. As illustrated, the stylet 28 is moved to the fully extended position, as seen in FIG. 1, for insertion into a patient, and may be retrieved rearwardly as seen in FIG. 2, to the fully retracted position, so that the stylet may be returned safely into the bore 14 of protector chamber 12 following its use.

Further, as is illustrated in the FIGURES, particularly FIG. 1, the inner most surface 15 of protector chamber 12 would include a plurality of detents 50. At the forward end, detents 50 are arranged in pairs to define a detent space 52 between each pair, for accommodating the forward most disc rail guide 42 within space 52 and lockingly engage the stylet body 34 therebetween, to assure that the stylet 28 is maintained in the fully extended position as seen in FIG. 1, during insertion into a patient. Likewise, as seen in FIGS. 2 and 5, following insertion, the stylet is retracted into the bore 14 of protector chamber 12, the distal disc rail guide 44 is lockingly engaged into a rear set of pairs of detents 56 and 58, so that when disc rail guide 44 is engaged between detents 56 and 58, defining a detent space 59, stylet body 34 together with stylet 28 affixed in engagement within the bore 14 of protector chamber 12, for disposal.

As illustrated in FIGURES, particularly FIGS. 2 and 7, during the retraction of stylet 28 into bore 14 of protector chamber 12, the stylet body 34 is disengaged from catheter 20, by pressure being applied with one's finger 60 onto the removal guide 62 on the upper portion of catheter hub 23, and following the retraction of stylet 28 in the bore 14 of protector chamber 12, the protector chamber 12 is removed therefrom with stylet 28 engaged within bore 14. Following the removal of catheter body 20 from stylet body 34, the plunger 16 would be threadably disengaged from stylet body 34, and a pair of cap members 64 and 67 (as seen in FIG. 7), would be slidably positioned upon the ends of protector chamber 12, while the stylet body 34 and stylet 28 are within bore 14 so that the protector chamber 12 for the caps 64 and 67 are engaged thereupon, and stylet 28 could be safely disposed without any regard for harm to a person who may subsequently become in contact with the disposed apparatus.

Figure 3:
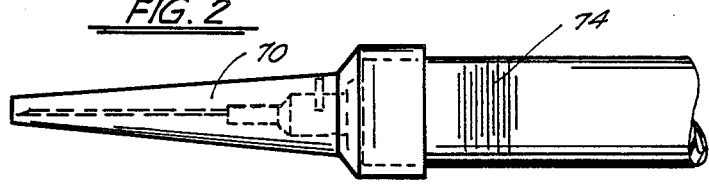
FIG. 3 is a partial view of the preferred embodiment of the apparatus of the present invention with an optional cap in position over the stylet and cannula while the stylet is in the extended position.
Figure 4:
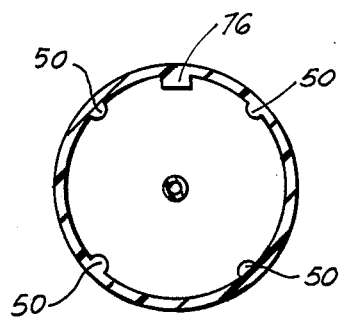
FIG. 4 is cross-section view along 4—4 in FIG. 2 illustrating the stop members for engaging the stylet when the stylet is in the fully extended position.

In FIG. 3 there is illustrated a cap portion 70 which may be slidably positioned onto catheter 20 or protector chamber 12 prior to the use of the apparatus, while the stylet is in the extended position as seen FIG. 1, so that upon removal of cap 70, having catheter receiving body 72 extending therefrom, the apparatus 10 may be utilized and for the purposes heretofore described. As further seen in FIG. 3 there is illustrated a series of ridges 74 along the outer wall 13 of protector chamber 12, so that one would have a better grip on protector chamber 12 during use of the apparatus.

Figure 5:
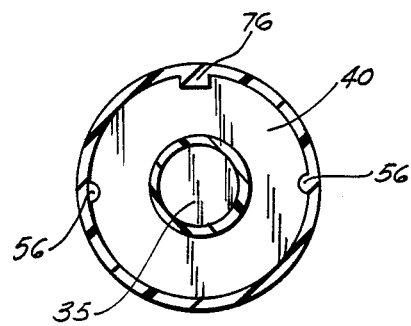
FIG. 5 is a view along lines 5—5 in FIG. 2 illustrating the stop members when the stylet is in the fully retracted position.
Figure 6:
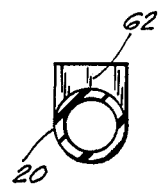
FIG. 6 is a cross-section view along lines 6—6 in FIG. 1 illustrating a catheter portion of the apparatus positioned on the end of the stylet body.

FIG. 5 would illustrate in cross-section view, a means for assuring that the beveled edge of the end of stylet 28 is in the up position during insertion of the stylet into the patient. This means would include a guide member 76, which is formed along the inner wall 15 of protector chamber 12, a guide member extending along the entire length of protector chamber 12 as illustrated in FIG. 2 in side view. As illustrated in FIG. 7, each disc rail guide 42 and 44 would include an indentation 78 along its face, with the indentation 78 being of sufficient width to accommodate guide 76. Therefore while the stylet body 34 and cannula 24 on stylet 28 are being moved to the extended position from FIG. 2 as illustrated in FIG. 1, the guide rail 76 would be positioned within indent 78, thus assuring that as the end of the stylet 28 extends out of the cannula 24 and the guide rail 76 is in the up or "12 O'Clock" position, the beveled edge 27 is likewise in that same position and would be ready for insertion into the patient.

Figure 8:
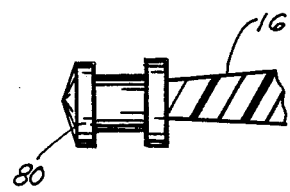
FIGS. 8 and 9 illustrate alternate means of connecting the stylet to the stylet body plunger.
Figure 9:
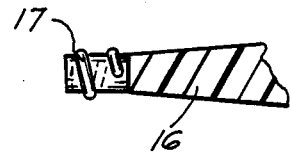

FIGS. 8 and 9 illustrate a pair of alternate plunger head attachments between the plunger head 16 and the stylet body 34 during use of the apparatus. In FIG. 9, the attachment is the threaded attachment as is illustrated in the principal embodiment, and in FIG. 8 there is illustrated an alternate attachment, having the plunger head inserted into the stylet body 34, so that in rare instances, blood may be drawn through the stylet into the stylet body 34 through the use of the plunger 80 moving within the receiving space 35 of stylet body receiving chamber 34. This would be an option included in the overall apparatus, and may be a manner in which blood can be extracted from the patient during use of the apparatus.

Because many varying and different embodiments may be made within the scope of the inventive concept herein taught, and because many modifications may be made in the embodiments herein detailed in accordance with the descriptive requirement of the law, it is to be understood that the details herein are to be interpreted as illustrative and not in a limiting sense.

What is claimed as invention is:

1. An intravenous catheter apparatus having a retractable stylet, the apparatus comprising:
    (a) a stylet comprising an elongated element, having a bore therethrough, the element including a first end insertable into a patient, and a second end attachable to a stylet body portion, the body portion defining a chamber for receiving a certain quantity of fluid flowing from the patient through the bore in the elongated element;
    (b) catheter means for receiving the stylet, including a hub portion engaged to the stylet body portion;
    (c) a protector chamber, housing the stylet body portion at all times while the stylet is moved from a first position extending through the catheter means, to a second position fully retracted into the protector chamber; and
    (d) means attachable to the stylet body portion for moving the stylet between the first extended position and the second retracted position.

2. The apparatus in claim 1, further comprising means for sealing the ends of the protector chamber, so that when the stylet is in the fully retracted position, the stylet is contained within the protector chamber.

3. The apparatus in claim 1, wherein the means for moving the stylet between the fully extended to the fully retracted position comprises a plunger attached to the stylet body.

4. The apparatus in claim 1, wherein there is further provided means positioned on an interior wall of the protector chamber for locking the stylet in the fully extended position.

5. The apparatus in claim 1, further comprising means on the interior wall of the protector chamber for locking the stylet in the fully retracted position.

6. The apparatus in claim 2, wherein the means for sealing the end portions of the protector chamber further comprises cap members positionable on first and second ends of the chamber after the stylet has been fully retracted into the chamber for shielding the stylet completely within the chamber.

7. The apparatus in claim 1, wherein there is further included a guide member along the interior surface of the protector chamber, for guiding the stylet through the catheter means so that a beveled end of the first end of the elongated element is in the up position when the guide member is in the up position.

8. The apparatus in claim 1, wherein the plunger is removable from the stylet prior to the ends of the protector chamber being sealed by the cap members.

9. An intravenous catheter apparatus, comprising:

(a) a stylet, including an elongated portion having a bore therethrough, a first end for insertion into a patient, and a second end portion;
(b) a stylet body, including a first end attachable to the stylet, and a second closed end, for receiving a limited amount of blood from the patient, collected through the bore in the elongated portion from the patient;
(c) a catheter, removably attached to a first end of the stylet body, the catheter having a bore therethrough for housing the stylet therein;
(d) a protector chamber, housing the stylet body during operation, as the stylet is moved from a first position extending through the catheter, to a second position fully retracted into the protector chamber; and
(e) means for moving the stylet between the first extended position while the stylet is inserted into the patient, to the second retracted position, after the stylet body has received the limited quantity of blood therein.

10. The apparatus in claim 9, wherein following the movement of the stylet to the fully retracted position, the catheter remains inserted into the patient for further use.

11. An intravenous catheter apparatus, comprising:
(a) a stylet, including an elongated portion having a bore therethrough, a first end for insertion into a patient, and a second end portion;
(b) a stylet body, having a first end secured to the second end of the elongated portion, and a second closed end, for receiving a limited amount of blood collected through the stylet from the patient;
(c) a catheter, removably attached to the first end of the stylet body; the catheter having a bore therethrough for housing the stylet therein;
(d) a protector chamber, housing the stylet body portion during operation, as the stylet is moved from a first position extending through the cannula, to a second position fully retracted into the protector chamber;
(e) means for moving the stylet between the first extended position inserted into the patient, to the second retracted position, after the stylet body has received the limited quantity of blood therein; and
(f) guide members positioned between the protector chamber and the stylet body for maintaining the stylet body centered within the chamber when the stylet is retracted into the protection chamber.

* * * * *